US006656172B1

(12) United States Patent
Hildebrand

(10) Patent No.: US 6,656,172 B1
(45) Date of Patent: Dec. 2, 2003

(54) METHOD FOR TREATING SEVERE TINNITUS

(75) Inventor: Keith Robert Hildebrand, Houlton, WI (US)

(73) Assignee: Medtronic, Inc., Minneapolis, MN (US)

(*) Notice: Subject to any disclaimer, the term of this patent is extended or adjusted under 35 U.S.C. 154(b) by 31 days.

(21) Appl. No.: 10/259,101

(22) Filed: Sep. 27, 2002

(51) Int. Cl.[7] .......................... A61K 9/22; A61B 19/00
(52) U.S. Cl. ..................... 604/891.1; 128/898
(58) Field of Search .................. 604/500, 28, 116, 604/891.1, 890.1, 151; 128/897–899

(56) References Cited

U.S. PATENT DOCUMENTS

| | | |
|---|---|---|
| 5,496,369 A | 3/1996 | Howard, III |
| 5,676,655 A | 10/1997 | Howard, III et al. |
| 5,713,847 A | 2/1998 | Howard, III et al. |
| 5,895,372 A * | 4/1999 | Zenner et al. ............... 604/93 |
| 6,358,926 B2 * | 3/2002 | Donovan ..................... 514/14 |
| 6,377,849 B1 * | 4/2002 | Lenzarz ....................... 604/21 |

OTHER PUBLICATIONS

Lewis, J.E., S.D.G. Stephens, et al. (1993). "Tinnitus and suicide." *Clin Otolaryngol* 19:50–54.
McFadden, D. (1982). *Tinnitus: Facts, Theories, and Treatments*. Washington D.C., National Academy Press.
Sataloff, J., R.T. Sataloff, et al. (1987). "Tinnitus and vertigo in healthy senior citizens without a history of noise exposure." *Am J Otol* 8 (2):87–89.
Axelsson, A. and A. Ringdahl (1989). "Tinnitus—a study of its prevalence and characteristics." *British Journal of Audiology* 23: 53–62.

Coles, R. R. A., Thompson, et al. (1992). "Intra–tympanic injections in the treatment of tinnitus." *Clin Otolaryngol* 17(3): 240–242.
Dobie, R.A. (1999). "A review of randomized clinical trials in tinnitus." *The Laryngoscope* 109: 1202–1211.
Lockwood, A.H., R.J. Salvi, et al. (1998). "The functional neuroanatomy of tinnitus: Evidence for limbic system links and neural plasticity." *Neurology* 50: 114–120.
Moller, A.R. (2001). "Symptoms and signs caused by neural plasticity." *Neurological Research* 23: 565–572.
Den Hartigh, J., C. G. J. M. Hilders, et al.(1993). "Tinnitus suppression by intravenous lidocaine in relation to its plasma concentration." *Clin Pharmaocol & Ther* 54:415–420.
Ochi, K. and J.J. Eggermont (1996). "Effects of salicylate on neural activity in cat primary auditory cortex." *Hearing Research* 95 (1–2): 63–76.
Caspary, D.M., J. C. Milbrandt, et al. (1995). "Central Auditory Aging: Gaba Changes in the Inferior Colliculus." *Experimental Gerontology* 30 (3/4):349–360.
McGeer, E. G. and P. L. McGeer (1975). "Age Changes in the Human for Some Enzymes Associated with Metabolism of the Catecholamines, Gaba and Acetycholine." *Neurobiology of Aging*. J. Ordy, Brizzee KR, New York, Plenum Pres: 287–305.
Raza, A., J. C. Milbrandt, et al. (1994). "Age–Related Changes in Brainstem Auditory Neurotransmitters: Measures of GABA and Acetylcholine Function." *Hear Res* 77 (1–2):221–230.

(List continued on next page.)

*Primary Examiner*—Sharon Kennedy
(74) *Attorney, Agent, or Firm*—Banner & Witcoff, Ltd.

(57) ABSTRACT

A method for treating severe tinnitus is disclosed. The method of the present invention comprises implanting a catheter into a patient and administering a therapeutic agent intrathecally into the patient's cerebrospinal fluid.

36 Claims, 5 Drawing Sheets

OTHER PUBLICATIONS

Araki, T., H. Kato, et al. (1993). "Selective changes of neurotransmitter receptors in middle–aged gerbil brain." *Neurochem Int* 23(6): 541–548.

Mildbrandt, J. C., R. L. Albin, et al. (1994). "Age–Related Decrease in GABAB Receptor Binding in the Fischer 344 Rat Inferior Colliculus." *Neurobiol Aging* 15(6): 699–703.

Moller, A. R., M. B. Moller, et al. (1992). "Some Forms of Tinnitus May Involve the Extralemniscal Auditory Pathway." *Laryngoscope* 102(10): 1165–1171.

Szczrpaniak, W. S. and A. R. Moller (1995). "Effects L–Baclofen and D–Bachlofen on the Auditory System: A Study of Click–Evoked Potentials from the Inferior Colliculus in the Rat." *Ann Otol Rhinol Laryngol* 104(5): 399–404.

Szczepaniak, W. S. and A. R. Moller (1996). "Effects of (–) baclofen, clonazepam, and diazepam on tone exposure–induced hyperexcitability of the inferior colliculus in the rat: possible therapeutic implications for pharmacological management of tinnitus and hyperacusis." *Hear Res* 97:46–53.

Lees, A. J., C. R. Clarke, et al. (1997). "Hallucinations After Withdrawal of Baclofen." *Lancet* 8016:858.

Zapp, J. J. (2001). "Gabapentin for the treatment of tinnitus: A case report." *ENT–Ear, Nose & Throat Journal*: 114–116.

Kuzniecky, R., S. Ho, et al. (2002). "Modulation of cerebral GABA by topiramate, lamotrigine, and gabapentin in healthy adults." *Neurology* 58: 368–372.

Petroff, O. A., F. Hyder, et al. (2000). "Effects of Gabapentin on Brain GABA, Homocarnosine, and Pyrrolydinone in Epilepsy Patients." *Epilepsia* 41(6): 675–680.

Westerberg, B. D., J. B. Roberson, et al. (1996). "A double–blind placeb–controlled trial of baclofen in the treatment of tinnitus." *Am J Otolaryngol* 17: 896–903.

Coffey, R. J., D. Cahill, et al. (1993). "Intrathecal baclofen for intractable spasticity of spinal origin: results of a long–term multicenter study." *J Neurosurg* 78: 226–232.

Meythaler, J. M., S. Guin–Renfroe, et al. (2001). "Continuously Infused Intrathecal Baclofen for Spastic/Dystonic Hempiplegia." *Arch Phys Med Rehabil* 82: 155–161.

Penn, R. D., S. M. Savoy, et al. (1989). "Intrathecal Baclofen for Severe Spinal Spasticity." *New England Journal of Medicine* 320: 1571–1521.

Knutsson, E., U. Lindblom, et al. (1974). "Plasma and Cerebraspinal Fluid Levels of Baclofen (Lioresal) at Optimal Therapeutic Responses in Spastic Paresis." *Journal of the neurological Sciences* 23: 473–484.

Kroin, J. S. (1992). "Intrathecal Drug Administration." *Clin Pharmacokinet* 22(5): 319–326.

Kroin, J. S. and R.D. Penn (1991). Cerebrospinal fluid pharmacokinetics of lumbar intrathecal baclofen. *Parenteral drug therapy in spasticity and parkinson's disease*. L. e. al. Carnforth, Parthenon Publishing: 67–77.

Muller, H., J. Zierski, et al. (1988). "Pharmacokinetics of Intrathecal Baclofen." *Local–spinal therapy of spasticity*. Z. J. Muller, H, Penn R.D. Berlin, Springer–Verlag: 223–226.

Milbrandt, JC, Holder TM, Wilson MC, Salvi RJ, Caspary DM. "GAD levels and muscimol binding in rat inferior colliculus following acoustic trauma." *Hear Res* (2000) Sep.; 147 (1–2):251–60.

Caspary, D.M., T.M. Holder, et al. "Age–Related Changes in GABA (A) Receptor Subunit Composition and Function in Rat Auditory System." *Neuroscience* 1999;93(1): 307–12.

Milbrandt JC, Hunter C, Caspary DM. "Alterations of $GABA_A$ Receptor Subunit mRNA Levels in the Aging Fischer 344 Rat Inferior Colliculus." *J Comp Neurol* (1997) Mar. 17; 379 (3):455–65.

Milbrandt JC, Albin RL, Turgeon SM, Caspary DM. "$GABA_A$ Receptor Binding in the Aging Rat Inferior Colliculus." *Neuroscience* (1996) Jul.; 73(2):449–58.

Simpson, J.J. and W.E. Davies (1999). "Recent advances in the pharmacological treatment of tinnitus." *TiPS* 20: 12–18.

Jastreboff, P.J., W.C. Gray, et al. (1996). "Neurophysiological approach to tinnitus patients." *Amer J Otol* 17: 236–240.

Merchant, S.N. and M.V. Kirtane (1986). "Vestibular effects of intravenous lidocaine used in the treatment of tinnitus." *J Laryngol Otol* 100:1249–1253.

Podoshin, L., M. Fradis, et al. (1992). "Treatment of tinnitus by intratympanic installation of lignocaine (lidocaine) 2 per cent through ventilation tubes." *J Laryngol Otal.* 106(7):603–606.

Raza, A., J.C. Mildbrandt (1994). "Age–related changes in brainstem auditory neurotransmitters: measures of GABA and acetylcholine function." *Hear Res* 77(1–2): 221–230.

Kaltenbach, J. A. (2000). "Neurophysiologic Mechanisms of Tinnitus." *J Am Acad Audiol* 11:125–137.

\* cited by examiner

METHOD FOR TREATING SEVERE TINNITUS

FIELD OF THE INVENTION

This invention relates to a method for treating severe tinnitus.

BACKGROUND OF THE INVENTION

Tinnitus is the perception of ringing, hissing, or other sounds in the ears or head when no external sound is present. For some people, tinnitus is just a nuisance. For others, it is a life-altering condition. According to the American Tinnitus Association, over 50 million Americans experience tinnitus to some degree and of these, approximately 12 million people have tinnitus to a distressing degree.

Approximately 2 million Americans have tinnitus to the point where they are so seriously debilitated that they cannot function on a "normal" day-to-day basis and some may commit suicide. Lewis, J. E., S. D. G. Stephens, et al. (1993). "Tinnitus and suicide." Clin Otolaryngol 19: 50–54. It is this severely affected population, which is only poorly managed with therapies available today, that may benefit from intrathecal pharmacotherapy proposed in the current investigation.

In terms of population percentages, approximately 17% of the general population, and 33% of the elderly population suffer from tinnitus. McFadden, D. (1982). Tinnitus: Facts, Theories, and Treatments. Washington D.C., National Academy Press; and Sataloff, J., R. T. Sataloff, et al. (1987). "Tinnitus and vertigo in healthy senior citizens without a history of noise exposure." Am J Otol 8(2): 87–89.

Axelsson and Ringdahl reported that approximately 2.5% of the tinnitus patients that they surveyed complained that tinnitus "plagued me all day." Axelsson, A. and A. Ringdahl (1989). "Tinnitus-a study of its prevalence and characteristics." British Journal of Audiology 23: 53–62. In Western countries various investigators have reported 0.5% to 1.0% of the population are severely affected by tinnitus to the extent that it interferes with their normal working and leisure life. Coles, R. R. A., A. C.

Thompson, et al. (1992). "Intra-tympanic injections in the treatment of tinnitus." Clin Otolaryngol 17(3): 240–242.

Despite the large medical impact of tinnitus, no widely accepted, effective treatment exists for the majority of cases of tinnitus. Dobie, R. A. (1999). "A review of randomized clinical trials in tinnitus." The Laryngoscope 109: 1202–1211; Simpson, J. J. and W. E. Davies (1999). "Recent advances in the pharmacological treatment of tinnitus." TiPS 20: 12–18.

In the vast majority of tinnitus cases an underlying cause is not apparent, and effective treatments (i.e., treatments which actually eliminate or reduce the sound) are not available. Most of the therapies that are presently available attempt to minimize the patients' awareness of the tinnitus symptoms or reduce their emotional reaction to their condition.

Rational treatment for the small proportion of patients with a reversible cause for their tinnitus involves correcting the underlying condition. This may involve removing or reducing the dose of the pharmacologic mediator (e.g., aspirin, aminoglycoside) or correcting the mechanical defect in the peripheral auditory system (e.g., remove obstructions in external auditory canal, surgically correct middle ear problems, or surgically decompress microvascular compressions of the auditory nerve).

Audiological Management

The most common method used to manage mild to moderate tinnitus is masking. In its simplest form, masking consists of self-exposure to background noise such as, radio, television, or recorded music. People with normal hearing and severe tinnitus can wear a small hearing-aid-like device that produces background (masking) noise in the affected ear. Patients with concomitant impaired hearing and tinnitus sometimes benefit (both their hearing and tinnitus) from use of a conventional hearing aid.

Psychotherapy

Limbic structures of the brain may be involved in the neural plastic changes associated with tinnitus. Supportive of this notion is the observation that the perceived amplitude of the tinnitus often does not correspond to the overall severity of the condition. For example, some patients with tinnitus of a relatively low volume are extremely disturbed, whereas others with high volume tinnitus are relatively unaffected by it. Lockwood, A. H., R. J. Salvi, et al. (1998). "The functional anatomy of gaze-evoked tinnitus: Evidence for limbic system links and neural plasticity." Neurology 50: 114–120.

Some researchers have used this observation to justify treatments based upon a habituation counseling strategy. Jastreboff, P. J., W. C. Gray, et al. (1996). "Neurophysiological approach to tinnitus patients." Amer J Otol 17: 236–240. Habituation is a psychological technique that trains patients to ignore or minimize their emotional reaction to tinnitus. Habituation is traditionally defined as the disappearance of reactions to sensory stimuli because of repetitive exposure and the lack of positive or negative reinforcement. A necessary condition for inducing habituation is to remove the association between tinnitus and the emotional state, i.e., to remove the activation of the limbic system by the tinnitus signal. The most popular version of this therapy, tinnitus retraining therapy, has been developed and popularized by Dr. Pawel Jastreboff. The process typically requires approximately 12 months of therapy. Treatments tend to be more successful for mild and moderate forms of tinnitus and for cases of shorter duration.

Psychoactive Drugs

The drugs most commonly used to manage tinnitus are antidepressants (especially tricyclics) and anxiolytics (valium, alprazolam, buspirone), although they have limited efficacy. Anxiolytics and antidepressants affect the secondary psychological sequelae of tinnitus, rather than the perception of the noise itself. The neural plasticity associated with tinnitus may involve the formation of new neural connections between the auditory and limbic systems of the brain. Moller, A. R. (2001). "Symptoms and signs caused by neural plasticity." Neurological Research 23: 565–572.

Although numerous other drugs have been tried, the majority of clinical trials have produced negative results. Dobie, R. A. (1999). "A review of randomized clinical trials in tinnitus." The Laryngoscope 109: 1202–1211. Most agents have been administered orally, although several clinical trials attempting to directly administer agents into the ear have also failed to show efficacy. Coles, R. R. A., A. C. Thompson, et al. (1992). "Intra-tympanic injections in the treatment of tinnitus." Clin Otolaryngol 17(3): 240–242.

Pharmacologic Tinnitolytic Agents

Lidocaine

Intravenously (IV) administered lidocaine is the only drug that has demonstrated consistent, significant, and reproducible efficacy against tinnitus. den Hartigh, J., C. G. J. M. Hilders, et al. (1993). "Tinnitus suppression by intravenous lidocaine in relation to its plasma concentration." *Clin Pharmaocol & Ther* 54: 415–420. Unlike other commonly prescribed oral medications that tend to manage only the emotional symptoms associated with tinnitus, lidocaine actually reduces or eliminates the noise. Lidocaine ameliorates tinnitus in approximately 60–80% of sufferers, a result that has been replicated in numerous well-controlled clinical trials. Merchant, S. N. and M. V. Kirtane (1986). "Vestibular effects of intravenous lidocaine used in the treatment of tinnitus." *J Laryngol Otol* 100: 1249–1253. The efficacy of IV lidocaine is greater than the efficacy produced by auditory nerve transection (approximately 50%), suggestive of a central mechanism of lidocaine action. However, locally administered lidocaine (to the ear or cochlea) has been relatively ineffective. In addition, locally administered lidocaine to the ear has been associated with significant vestibular side effects such as vertigo and nausea. Ochi, K. and J. J. Eggermont (1996). "Effects of salicylate on neural activity in cat primary auditory cortex." *Hearing Research* 95(1–2): 63–76; Podoshin, L., M. Fradis, et al. (1992). "Treatment of tinnitus by intratympanic installation of lignocaine (lidocaine) 2 percent through ventilation tubes." *J Laryngol Otol* 106(7): 603–606.

Despite the efficacy of IV lidocaine, it unfortunately does not represent a clinically useful therapy. Tinnitus patients effectively treated with IV lidocaine in the short term, usually experience a return of their symptoms shortly after the medication has been stopped. Intravenous lidocaine (bolus administration) has a short duration of action (10–20 minutes) and is metabolized rapidly by the liver (terminal half life of 1.5 to 2 hours in humans). Lidocaine used in the treatment of cardiac arrhythmias is typically diluted with saline, and administered as a precisely-metered IV infusion. Unfortunately in tinnitus patients with healthy heart rhythms, IV lidocaine can induce potentially life-threatening cardiac arrhythmias. Intravenous lidocaine at effective doses also can cause nausea and dizziness. If administered orally, lidocaine is ineffective due to a major first pass effect.

Baclofen

Tinnitus is associated with abnormal spontaneous neural activity at multiple levels within the central auditory pathways. Gamma-amino-butyric acid (GABA) is the main inhibitory neurotransmitter of the mammalian CNS. An example of a $GABA_B$-receptor agonist is baclofen, which mimics in part the effects of GABA.

Several studies have correlated age-related changes in the concentrations of GABA and $GABA_B$-binding sites in the Inferior Colliculus ("IC"), the major auditory midbrain structure. Caspary, D. M., J. C. Milbrandt, et al. (1995). "Central auditory aging: GABA changes in the inferior colliculus." *Experimental Gerontology* 30(3/4): 349–360; Raza, A., J. C. Milbrandt, et al. (1994). "Age-related changes in brainstem auditory neurotransmitters: measures of GABA and acetylcholine function." *Hear Res* 77(1–2): 221–230. Age-related decreases in the enzyme responsible for GABA synthesis (glutamic acid decarboxylase) have been reported in the IC of both rats and humans. McGeer, E. G. and P. L. McGeer (1975). Age changes in the human for some enzymes associated with metabolism of the catecholamines, GABA and acetycholine. *Neurobioloby of Aging*. J. Ordy, Brizzee KR. N.Y., Plenum Press: 287–305; Raza, A., J. C. Milbrandt, et al. (1994). "Age-related changes in brainstem auditory neurotransmitters: measures of GABA and acetylcholine function." *Hear Res* 77(1–2): 221–230. In rats, age-related decreases in the levels of GABA and the number of $GABA_B$-binding sites within the IC have also been reported. Araki, T., H. Kato, et al. (1993). "Selective changes of neurotransmitter receptors in middle-aged gerbil brain." *Neurochem Int* 23(6): 541–548; Milbrandt, J. C., R. L. Albin, et al. (1994). "Age-related decrease in GABAB receptor binding in the fischer 344 rat inferior colliculus." *Neurobiol Aging* 15(6): 699–703. These biochemical findings may explain why tinnitus is more prevalent among the elderly.

In addition to age-related biochemical changes, the inferior colliculus also shows changes in function (increased spontaneous activity) in response to noise exposure or injury to the peripheral auditory system, results commonly associated with tinnitus in humans. Moller, A. R., M. B. Moller, et al. (1992). "Some forms of tinnitus may involve the extralemniscal auditory pathway." *Laryngoscope* 102(10): 1165–1171. In rats, IV baclofen inhibited noise-induced electrical potentials recorded directly from IC neurons. Szcepaniak, W. S. and A. R. Moller (1995). "Effects L-baclofen and D-baclofen on the auditory system: a study of click-evoked potentials from the inferior colliculus in the rat." *Ann Otol Rhinol Laryngol* 104(5): 399–404; Szcepaniak, W. S. and A. R. Moller (1996). "Effects of (−) baclofen, clonazepam, and diazepam on tone exposure-induced hyperexcitability of the inferior colliculus in the rat: Possible therapeutic implications for pharmacological management of tinnitus and hyperacusis." *Hear Res* 97: 46–53. An additional observation suggestive of the inhibitory role of GABA in the normal auditory system comes from clinical reports of auditory hallucinations that are sometimes experienced with baclofen withdrawal in humans. Lees, A. J., C. R. Clarke, et al. (1977). "Hallucinations after withdrawal of baclofen." *Lancet* 8016: 858.

Additional evidence that may implicate GABA in the pathophysiology of tinnitus are: 1) Benzodiazepines are often used with moderate efficacy to treat tinnitus. As sedatives, they may reduce the stress associated with tinnitus. However, benzodiazepine-mediated modulation of $GABA_A$ receptors may also be involved. 2) Anecdotal reports describe the efficacy of gabapentin in tinnitus patients. Zapp, J. J. (2001). "Gabapentin for the treatment of tinnitus: A case report." *ENT-Ear, Nose & Throat Journal*: 114–116. Although the precise molecular mechanisms of gabapentin remain elusive, it is generally believed that gabapentin augments central GABA functions either by promoting its release and/or inhibiting its degradation. Kuzniecky, R., S. Ho, et al. (2002). "Modulation of cerebral GABA by topiramate, lamotrigine, and gabapentin in healthy adults." *Neurology* 58: 368–372; Petroff, O. A., F. Hyder, et al. (2000). "Effects of gabapentin on brain GABA, homocamosine, and pyrrolidinone in epilepsy patients." *Epilepsia* 41(6): 675–680.

In light of the above preclinical data, a single placebo controlled human clinical trial was conducted to evaluate the efficacy of oral baclofen ($\leq 60$ mg/day) to treat tinnitus. Westerberg, B. D., J. B. Roberson, et al. (1996). "A double-blind placeb-controlled trial of baclofen in the treatment of tinnitus." *Am J Otolaryngol* 17: 896–903. The authors conducted a randomized, double-blinded study after anecdotal reports described patients who experienced beneficial subjective reduction in tinnitus while taking oral baclofen. The clinical trial used oral baclofen, up to 60 mg/day, in patients with chronic tinnitus. Not all of the patients had severe tinnitus, and for some, tinnitus was not their primary complaint. After a 3-week course of escalating doses (20 mg/day×1 week; then 40 mg/day×1 week; then 60 mg/day ×1 week) subjects were retested using the Tinnitus Handicap Inventory, loudness and pitch matching, and maskability of tinnitus using white noise. Subjective improvement in tinnitus occurred in only 9.7% of baclofen-treated patients as opposed to 3.4% in placebo-treated patients. This outcome was not statistically significant. Oral baclofen therapy was associated with significant side effects that included sedation, confusion, dizziness, GI upset, and weakness, the combination of which caused 25% of the enrolled patients to drop out of the trial.

These side effects are also associated with oral baclofen used to treat spasticity but are typically not a problem when baclofen is administered intrathecally to treat spasiticity. Coffey, R. J., D. Cahill, et al. (1993). "Intrathecal baclofen for intractable spasticity of spinal origin: results of a long-term multcenter study." *J Neurosurg* 78: 226–232; Meythaler, J. M., S. Guin-Renfroe, et al. (2001). "Continuously infused intrathecal baclofen over 12 months for spastic hypertonia in adolescents and adults with cerebral palsy." *Arch Phys Med Rehabil* 82: 155–161; Penn, R. D., S. M. Savoy, et al. (1989). "Intrathecal baclofen for severe spinal spasticity." *New England Journal of Medicine* 320: 1571–1521.

U.S. Pat. No. 5,676,655 discloses a method for implanting a neural prosthetic drug delivery apparatus into a target zone of a patient's brain for reducing or eliminating the effects of tinnitus. The apparatus includes a catheter that is inserted into the patient's auditory cortex or thalamus. The catheter microinfuses drugs that suppress or eliminate abnormal neural activity into geometrically separate locations of the patient's cortex or thalamus, thereby reducing or eliminating the effects of tinnitus. The patent, however, deals with drug delivery directly into brain tissue or into specific anatomical structures, i.e. intraparenchymal drug delivery. There are a number of disadvantages to intraparenchymal drug delivery to treat severe tinnitus. For example, intraparenchymal drug delivery is relatively invasive and requires a highly trained neurosurgeon to implant the catheter into the brain tissue or specific anatomical structure.

SUMMARY OF THE INVENTION

One or more of the above-mentioned deficiencies in the art are satisfied by the method of the present invention of intrathecal drug delivery for the treatment of severe tinnitus. One embodiment of the invention involves the use of one or more therapeutic agents intrathecally to treat tinnitus. For example, a catheter is implanted into a patient, the catheter having a proximal end and a distal end. The distal end of the catheter is adapted to infuse at least one therapeutic agent intrathecally into a patient's cerebrospinal fluid. The therapeutic agent or agents may comprise a local anesthetic such as lidocaine or bupivacaine, a GABA agonist such as baclofen or muscimol, or a serotonin agonist such as sumatriptan.

In one embodiment of the invention, the proximal end of the catheter is coupled to an implantable pump and the distal end of the catheter is inserted into the subarachnoid space of a patient's spinal column. The implantable pump is operated to deliver at least one therapeutic agent through the distal end and directly into the cerebrospinal fluid contained in the subarachnoid space of the patient's spinal column. The therapeutic agent or agents may comprise a local anesthetic such as lidocaine or bupivacaine, a GABA agonist such as baclofen or muscimol, or a serotonin agonist such as sumatriptan.

These and other advantages and features of the invention will become apparent upon reading and following the detailed description and referring to the accompanying drawings which like numbers refer to like parts throughout.

DETAILED DESCRIPTION OF THE PREFERRED EMBODIMENTS

Figure 1:
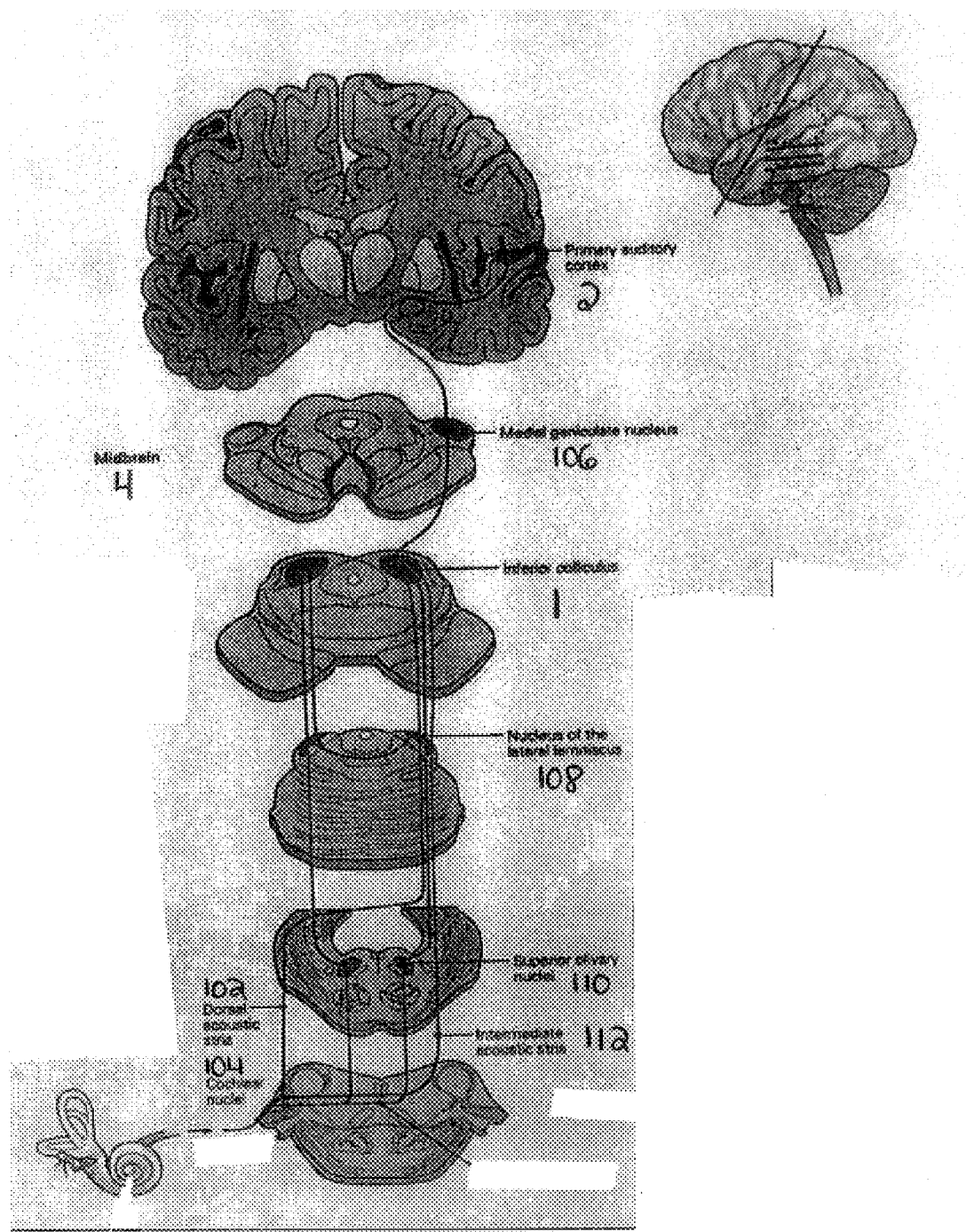
FIG. 1 is a diagrammatic illustration of the central auditory pathways.
Figure 2:
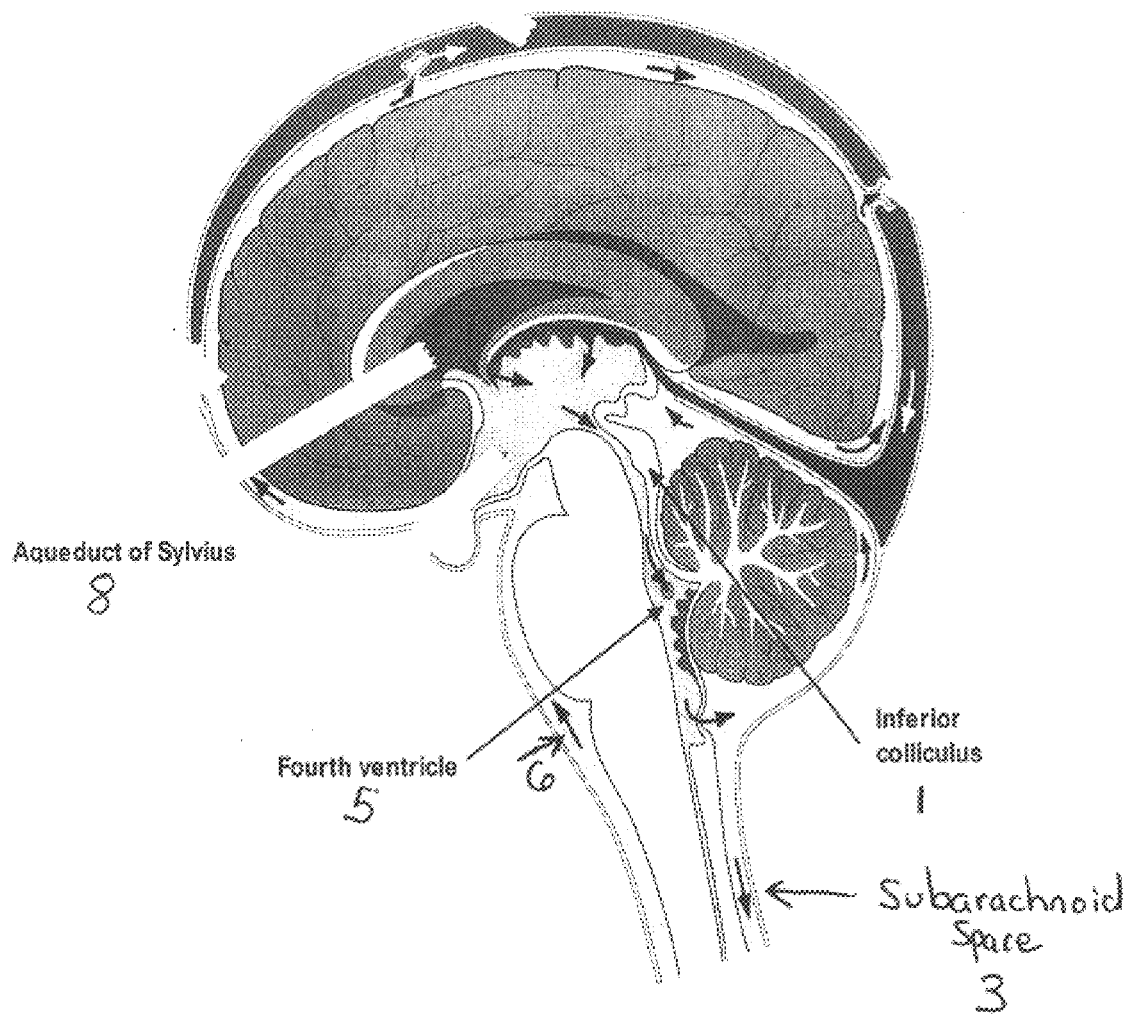
FIG. 2 is a diagrammatic illustration of the location of a patient's inferior colliculus and the flow of cerebrospinal fluid in the subarachnoid space.

As illustrated in FIG. 1, the central auditory pathways comprise, the inferior colliculus 1, the auditory cortex 2, the dorsal acoustic stria 102, the cochlear nuclei 104, the geniculate nucleus 106, the nucleus of the lateral lemniscus 108, the superior olivary nuclei 110, and the intermediate acoustic stria 112. Experimental evidence suggests that the dorsal cochlear nuclei 104, the inferior colliculus 1, and the auditory cortex 2, as shown in FIGS. 1 and 2, may be involved in the generation of tinnitus. Kaltenbach, J. A. (2000). "Neurophysiologic mechanisms of tinnitus." *J Am Acad Audiol* 11: 125–137. These major auditory structures are relatively shallow brain structures that lie in close proximity to the subarachnoid space 3 as shown in FIG. 2.

The inferior colliculus 1 lies on the dorsal surface of the midbrain 4 and rostral (cephalad) to the fourth ventricle 5 and dorsal to the cerebral aqueduct of Sylvius 8. The superficial surface of the inferior colliculus 1 is bathed in cerebrospinal fluid (CSF) 6 that exits the foramina of Magendie and Luschka to flow around the brainstem and cerebellum. The arrows within the subarachnoid space 3 in FIG. 2 indicate cerebrospinal fluid 6 flow.

The subarachnoid space 3 is a compartment within the central nervous system that contains cerebrospinal fluid 6. The cerebrospinal fluid 6 is produced in the ventricular system of the brain and communicates freely with the subarachnoid space 3 via the foramina of Magendie and Luschka.

As previously discussed in the background of the invention, available evidence suggests that tinnitus arises within the central auditory structures of the brain, and that those structures represent an important target for therapeutic agents. Given the limited efficacy of other treatments, intrathecal delivery of therapeutics into the cerebrospinal fluid 6 in accordance with the present invention offers the potential to reduce the perception of tinnitus in a large portion of severely affected patients who currently have very limited options.

Additionally, intrathecal delivery of therapeutics into the cerebrospinal fluid is less invasive than intraparenchymal (direct tissue) delivery of therapeutics. In addition, intrathecal delivery of therapeutics may not require the need for a neurosurgeon as the delivery of the therapeutics does not require delivery to a direct brain target. Numerous other physicians may be qualified to insert a catheter into the lumbar subarachnoid space of the spinal column in order to initiate intrathecal therapeutic delivery.

Figure 3:
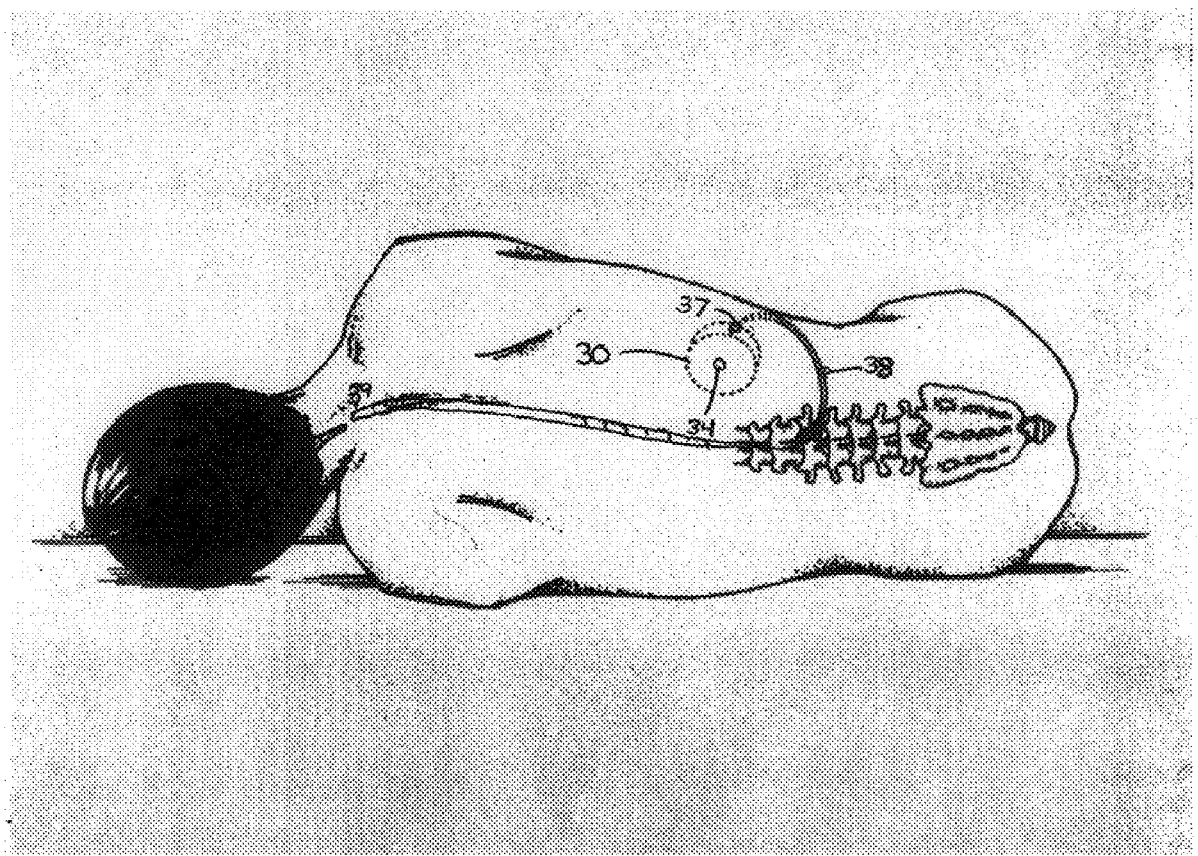
FIG. 3 is diagrammatic illustration of a catheter implanted in a patient according to an embodiment of the present invention.
Figure 5:
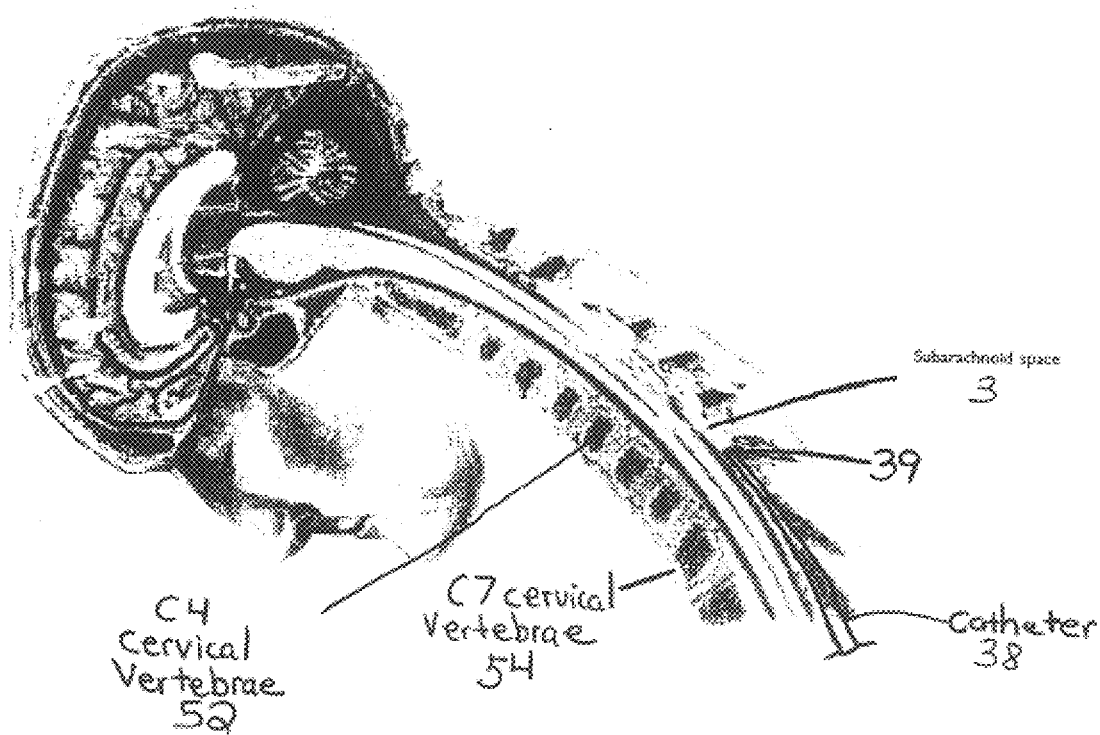
FIG. 5 is a diagrammatic illustration of a catheter implanted in a patient's subarachnoid space for the delivery of a therapeutic agent or agents into the cerebrospinal fluid.
Figure 1:
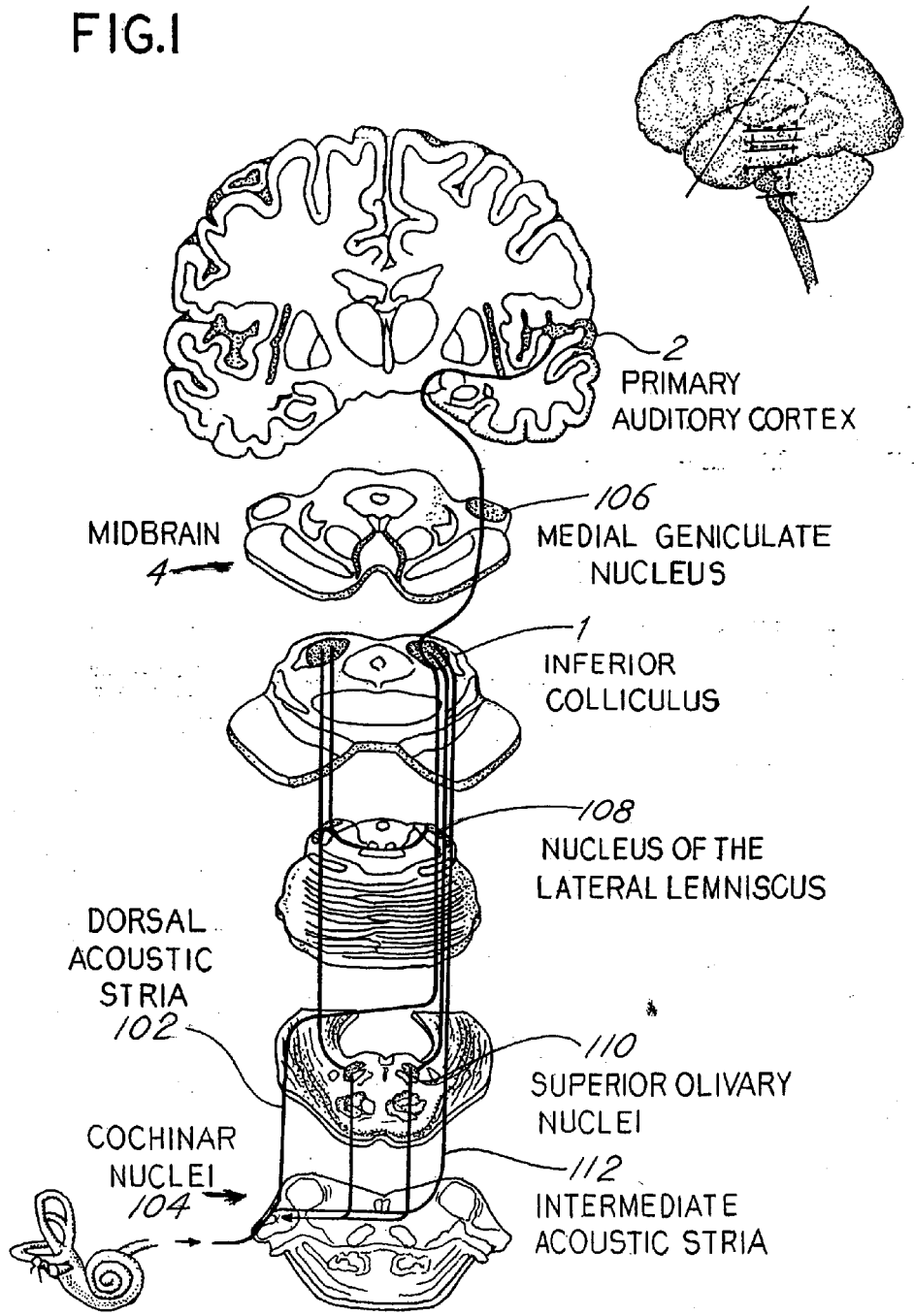
Figure 2:
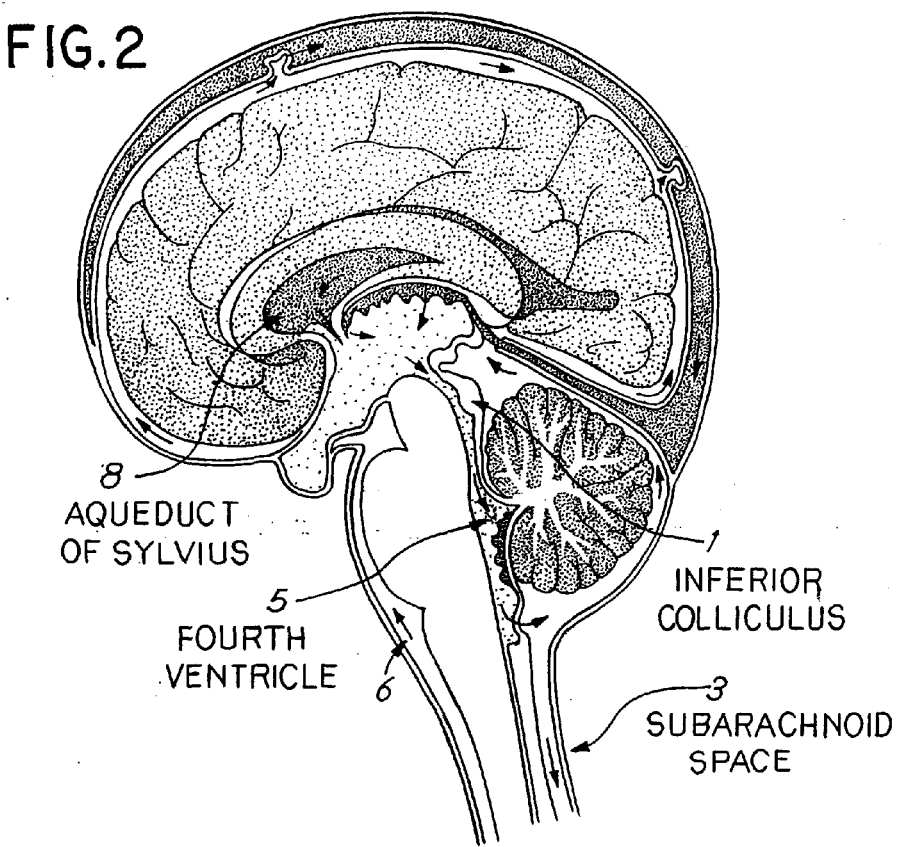
Figure 3:
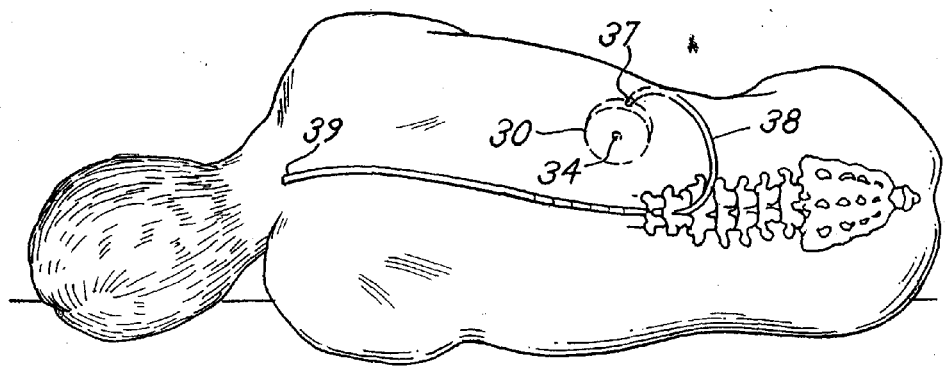
Figure 4:
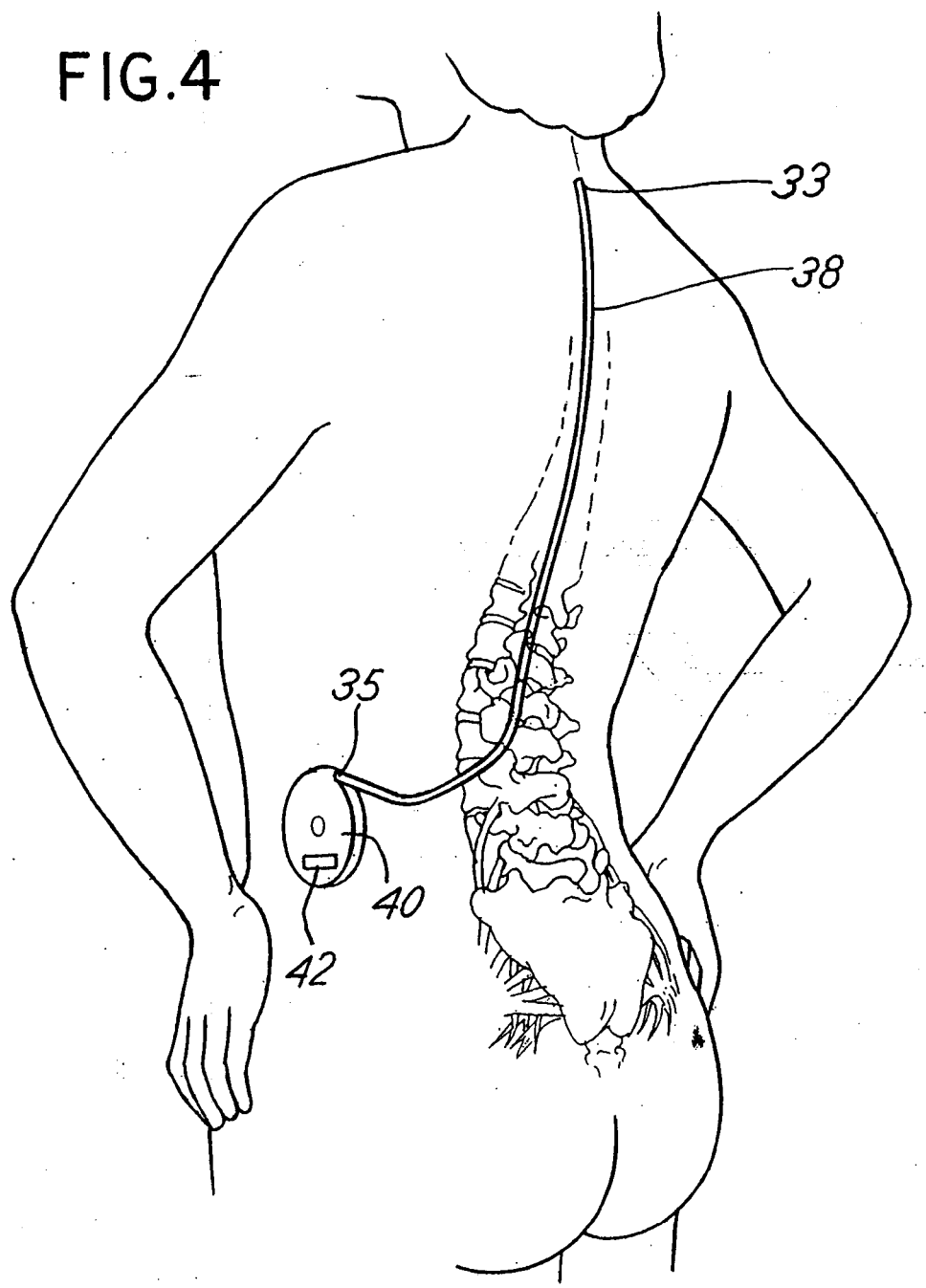
Figure 5:
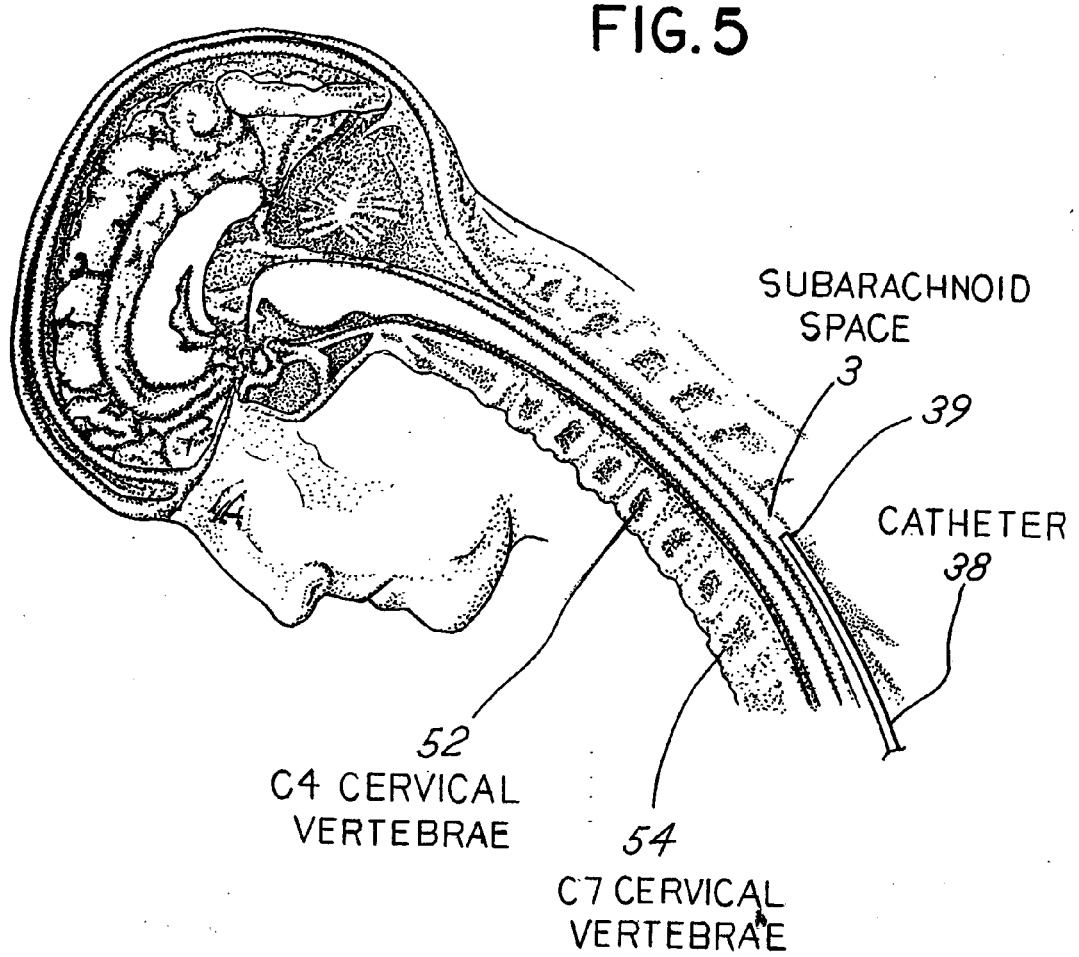

Referring to FIG. 3, a system or device 30 may be implanted below the skin of a patient. The device 30 has a port 34 into which a hypodermic needle can be inserted through the skin to inject a quantity of therapeutic agent. The therapeutic agent is delivered from device 30 through a catheter port 37 into a catheter 38. Catheter 38 is positioned so that the distal tip 39 of catheter 38 is positioned in the subarachnoid space 3 between the fourth cervical vertebrae (C4) 52 and the seventh cervical vertebrae (C7) 54, as shown in FIG. 5. The distal tip 39 can be placed in a multitude of locations to deliver a therapeutic agent into the cerebrospinal fluid of the patient. In a preferred embodiment, the distal tip 39 of catheter 38 is inserted in the subarachnoid space 3 between the fourth cervical vertebrae (C4) 52, and the seventh cervical vertebrae (C7) 54, to allow for relatively high therapeutic dose infusion concentrations in the intracranial CSF compartment near the inferior colliculus 1 while minimizing spinal exposure. While device 30 is shown in FIG. 3, delivery of a therapeutic agent into the CSF to treat severe tinnitus can be accomplished by simply injecting the therapeutic agent via port 34 to catheter 38.

A higher concentration of baclofen delivered intrathecally into the CSF in accordance with the present invention can provide improved reduction of the perception of tinnitus in a large proportion of severely effected patients. Baclofen is a zwitterionic, hydrophilic molecule that does not readily penetrate the blood-brain barrier. The enhanced efficacy and reduced side effects associated with baclofen delivered intrathecally provides higher concentrations of baclofen in CSF than baclofen delivered orally. For example, pharmacokinetic data shows that baclofen levels in the cisternal CSF, at the base of the brain, after lumbar intrathecal administration are approximately 20–30 times higher in the CSF than levels after oral administration to treat spasticity. Knutsson, E., U. Lindblom, et al. (1974). "Plasma and cerebraspinal fluid levels of baclofen (Lioresal) at optimal therapeutic responses in spastic paresis." *Journal of the neurological Sciences* 23: 473–484. Kroin, J. S. (1992). "Intrathecal drug administration." *Clin Pharmacokinet* 22(5): 319–326. Kroin, J. S. and R. D. Penn (1991). Cerebrospinal fluid pharmacokinetics of lumbar intrathecal baclofen. *Parenteral drug therapy in spasticity and parkinson's disease*. L. e. al. Carnforth, Parthenon Publishing: 67–77. Muller, H., J. Zierski, et al. (1988). Pharmacokinetics of intrathecal baclofen. *Local-spinal therapy of spasticity*. Z. J. Muller H, Penn RD. Berlin, Springer-Verlag: 223–226.

Another GABA agonist muscimol may also be intrathecally delivered into the CSF as a therapeutic agent alone or in combination with other therapeutic agents in an attempt to decrease the aberrant neural activity associated with tinnitus. Unlike baclofen, which is a selective $GABA_B$ agonist, muscimol is a selective $GABA_A$ agonist that inhibits neuronal activity by activating chloride channels leading to neuronal hyperpolarization.

Similarly, local anesthetics such as lidocaine or bupivacaine may also be intrathecally delivered into the CSF as a therapeutic agent alone or in combination with other therapeutic agents in an attempt to decrease the aberrant neural activity associated with tinnitus.

Additionally, a serotonin agonist such as sumatripatan may also be intrathecally delivered into the CSF as a therapeutic agent alone or in combination with other therapeutic agents in an attempt to decrease the aberrant neural activity associated with tinnitus.

Figure 4:
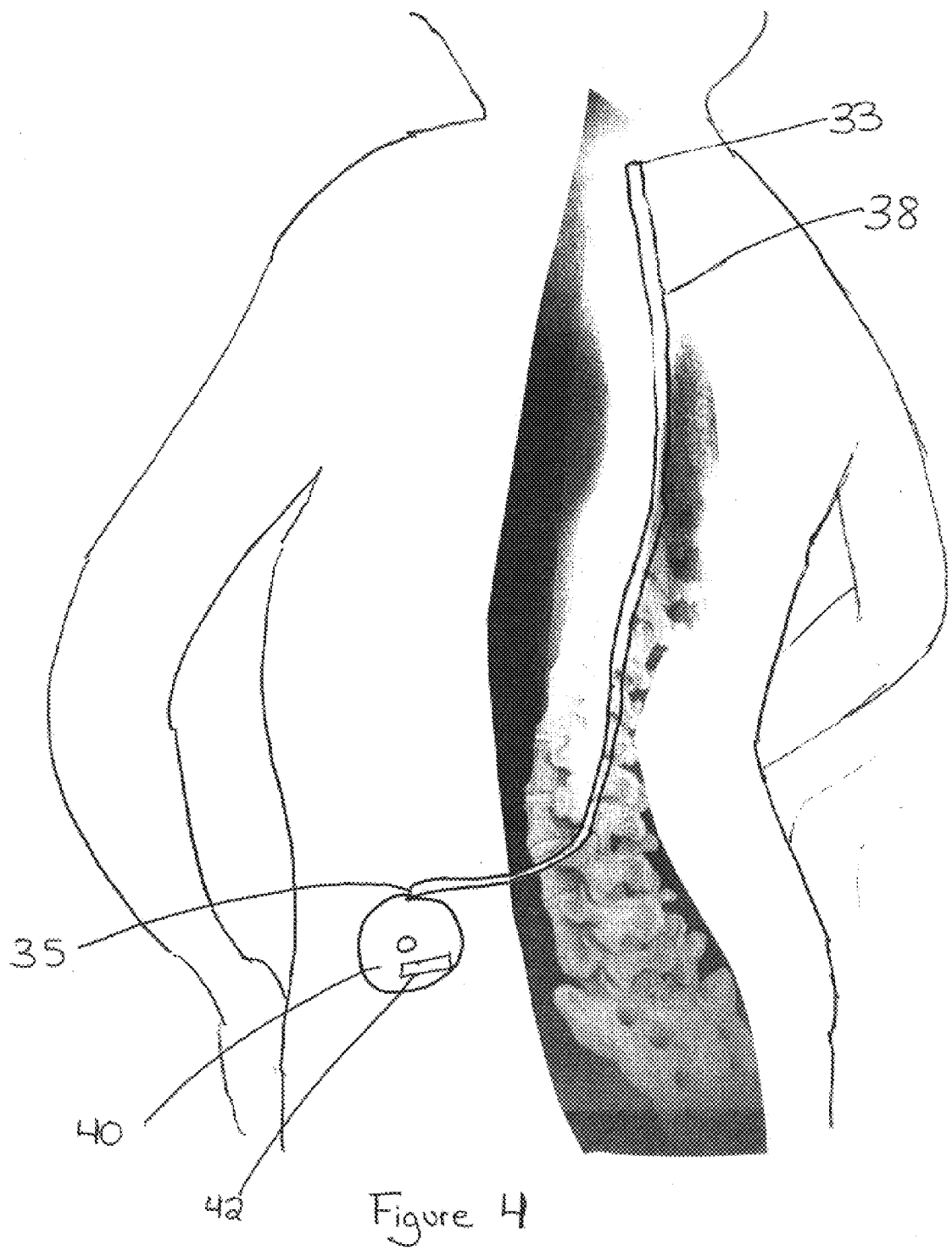
FIG. 4 is a diagrammatic illustration of an implanted catheter and pump in accordance with an embodiment of the present invention.

Referring to FIG. 4, an implantable medical device known as an implantable therapeutic pump 40 is implanted into a patient. The location of pump implantation is one in which the implantation interferes as little as practicable with patient activity, such as subcutaneous in the lower abdomen. The proximal end 35 of a catheter 38 is connected to the implantable therapeutic pump outlet. The catheter 38 is a flexible tube with a lumen typically runmning the length of the catheter 38. The distal end 33 of catheter 38 is positioned to infuse a therapeutic agent or agents into the target area of CSF of the patient. The target area of CSF of the patient may be the subarachnoid space 3 between the fourth cervical vertebrae (C4) 52 and seventh cervical vertebrae (C7) 54, as shown in FIG. 5. The implantable therapeutic pump 40 is operated to discharge a predetermined dosage of therapeutic or therapeutics into the CSF of the patient.

The implantable therapeutic pump 40 contains a microprocessor 42 or similar device that can be programmed to control the amount of therapeutic delivery. The programming may be accomplished with an external programmer/control unit via telemetry. The controlled amount of therapeutic or therapeutics may be delivered over a specified time period. With the use of the implantable therapeutic pump 40, different dosage regimens may be programmed for a particular patient. Additionally, different therapeutic dosages can be programmed for different combination of therapeutics. For example, in the case of the therapeutic baclofen, a dosage regimen may be initiated at the rate of 25 mcg/day (1.04 mcg/hr as an infusion). This dosage represents a conservative starting dose in that it is four times less than the lowest amount of baclofen injection, by labeling, that would be administered as a single intrathecal bolus for screening patients with movement disorders. Those skilled in the art will recognize that this approach will allow starring conservatively with lower doses and adjusting to a more aggressive dosing scheme, if warranted, based on safety and efficacy factors.

The embodiments of the invention, and the invention itself, are now described in such full, clear, concise and exact terms to enable a person of ordinary skill in the art to make and use the invention. To particularly point out and distinctly claim the subject matters regarded as invention, the following claims conclude this specification. To the extent variations from the preferred embodiments fall within the limits of the claims, they are considered to be part of the invention, and claimed.

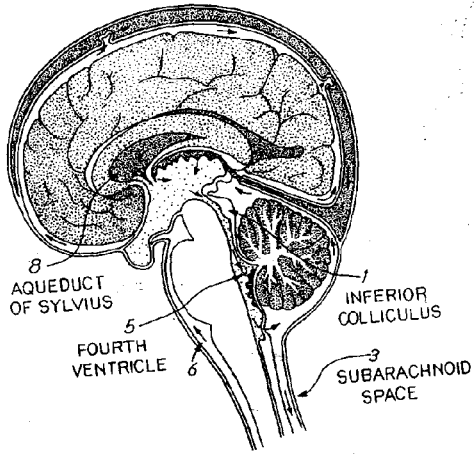

I claim:

1. A method of treating tinnitus, the method comprising:
   implanting a catheter having a proximal end and a distal end, the distal end adapted to infuse at least one therapeutic agent intrathecally into a patient's cerebrospinal fluid; and
   infusing the at least one therapeutic agent through the distal end of the catheter.

2. The method of claim 1, wherein the at least one therapeutic agent comprises a local anesthetic.

3. The method of claim 2, wherein the local anesthetic comprises lidocaine.

4. The method of claim 2, wherein the local anesthetic comprises bupivacaine.

5. The method of claim 1, wherein the at least one therapeutic agent comprises a GABA agonist.

6. The method of claim 5, wherein the GABA agonist comprises a $GABA_B$ agonist.

7. The method of claim 6, wherein the $GABA_B$ agonist comprises baclofen.

8. The method of claim 5, wherein the GABA agonist comprises a $GABA_A$ agonist.

9. The method of claim 8, wherein the $GABA_A$ agonist comprises muscimol.

10. The method of claim 1, wherein the at least one therapeutic agent comprises a serotonin agonist.

11. The method of claim 10, wherein the serotonin agonist comprises sumatriptan.

12. The method of claim 1, wherein the distal end of the catheter is placed in the subarachnoid space between the fourth and the seventh cervical vertebrae.

13. A method of treating tinnitus by means of an implantable pump and a catheter, the catheter having a proximal end coupled to the implantable pump and a distal end for infusing at least one therapeutic agent, the method comprising the steps of:

surgically implanting the catheter so that the distal end of the catheter is located in cerebrospinal fluid of a patient; and operating the implantable pump to discharge a predetermined dosage of the at least one therapeutic agent into the cerebrospinal fluid of the patient whereby the tinnitus is treated by intrathecal infusion.

14. The method of claim 13, wherein the distal end of the catheter is located in the subarachnoid space between a fourth and seventh cervical vertebrae.

15. The method of claim 13, wherein the at least one therapeutic agent comprises a local anesthetic.

16. The method of claim 15, wherein the local anesthetic comprises lidocaine.

17. The method of claim 15, wherein the local anesthetic comprises bupivacaine.

18. The method of claim 13, wherein the at least one therapeutic agent comprises a GABA agonist.

19. The method of claim 18, wherein the GABA agonist comprises a $GABA_B$ agonist.

20. The method of claim 19, wherein the $GABA_B$ agonist comprises baclofen.

21. The method of claim 18, wherein the GABA agonist comprises a $GABA_A$ agonist.

22. The method of claim 21, wherein the $GABA_A$ agonist comprises muscimol.

23. The method of claim 13, wherein the at least one therapeutic agent comprises a serotonin agonist.

24. The method of claim 23, wherein the serotonin agonist comprises sumatriptan.

25. A method of using at least one therapeutic agent to treat tinnitus, the method comprising:

implanting a catheter having a proximal end coupled to a pump and a distal end inserted into the subarachnoid space of a patients spinal column; and operating the pump to deliver the at least one therapeutic agent directly into the cerebrospinal fluid contained in the subarachnoid space of the patients spinal column.

26. The method of claim 25, wherein the at least one therapeutic agent comprises a local anesthetic.

27. The method of claim 26, wherein the local anesthetic comprises lidocaine.

28. The method of claim 26, wherein the local anesthetic comprises bupivacaine.

29. The method of claim 25, wherein the at least one therapeutic agent comprises a GABA agonist.

30. The method of claim 29, wherein the GABA agonist comprises a $GABA_B$ agonist.

31. The method of claim 30, wherein the $GABA_B$ agonist comprises baclofen.

32. The method of claim 29, wherein the GABA agonist comprises a $GABA_A$ agonist.

33. The method of claim 32, wherein the $GABA_A$ agonist comprises muscimol.

34. The method of claim 25, wherein the at least one therapeutic agent comprises a serotonin agonist.

35. The method of claim 34, wherein the serotonin agonist comprises sumatriptan.

36. The method of claim 25, wherein the catheter is placed in the subarachnoid space of a patients spinal column between a fourth and seventh cervical vertebrae.

* * * * *

UNITED STATES PATENT AND TRADEMARK OFFICE
CERTIFICATE OF CORRECTION

PATENT NO.    : 6,656,172 B1
DATED         : December 2, 2003
INVENTOR(S)   : Hildebrand It is certified that error appears in the above-identified patent and that said Letters Patent is hereby corrected as shown below:

The title page, showing an illustration figure, should be deleted and substituted therefor the attached title page.

Delete figures 1-5, and substitute therefor figures consisting of figures 1-5, as shown on the attached pages.

Signed and Sealed this

Twenty-fourth Day of August, 2004

JON W. DUDAS
*Director of the United States Patent and Trademark Office*

(12) United States Patent
Hildebrand

(10) Patent No.: US 6,656,172 B1
(45) Date of Patent: Dec. 2, 2003

(54) METHOD FOR TREATING SEVERE TINNITUS

(75) Inventor: Keith Robert Hildebrand, Houlton, WI (US)

(73) Assignee: Medtronic, Inc., Minneapolis, MN (US)

( * ) Notice: Subject to any disclaimer, the term of this patent is extended or adjusted under 35 U.S.C. 154(b) by 31 days.

(21) Appl. No.: 10/259,101

(22) Filed: Sep. 27, 2002

(51) Int. Cl.$^7$ .......................... A61K 9/22; A61B 19/00
(52) U.S. Cl. .................................. 604/891.1; 128/898
(58) Field of Search .......................... 604/500, 28, 116, 604/891.1, 890.1, 151; 128/897–899

(56) References Cited

U.S. PATENT DOCUMENTS

| | | | |
|---|---|---|---|
| 5,496,369 A | | 3/1996 | Howard, III |
| 5,676,655 A | | 10/1997 | Howard, III et al. |
| 5,713,847 A | | 2/1998 | Howard, III et al. |
| 5,895,372 A | * | 4/1999 | Zenner et al. ................. 604/93 |
| 6,358,926 B2 | * | 3/2002 | Donovan ....................... 514/14 |
| 6,377,849 B1 | * | 4/2002 | Lenzarz ......................... 604/21 |

OTHER PUBLICATIONS

Lewis, J.E., S.D.G. Stephens, et al. (1993). "Tinnitus and suicide." *Clin Otolaryngol* 19:50–54.
McFadden, D. (1982). *Tinnitus: Facts, Theories, and Treatments*. Washington D.C., National Academy Press.
Sataloff, J., R.T. Sataloff, et al. (1987). "Tinnitus and vertigo in healthy senior citizens without a history of noise exposure." *Am J Otol* 8 (2):87–89.
Axelsson, A. and A. Ringdahl (1989). "Tinnitus—a study of its prevalence and characteristics." *British Journal of Audiology* 23: 53–62.
Coles, R. R. A., Thompson, et al. (1992). "Intra–tympanic injections in the treatment of tinnitus." *Clin Otolaryngol* 17(3): 240–242.
Dobie, R.A. (1999). "A review of randomized clinical trials in tinnitus." *The Laryngoscope* 109: 1202–1211.
Lockwood, A.H., R.J. Salvi, et al. (1998). "The functional neuroanatomy of tinnitus: Evidence for limbic system links and neural plasticity." *Neurology* 50: 114–120.
Moller, A.R. (2001). "Symptoms and signs caused by neural plasticity." *Neurological Research* 23: 565–572.
Den Hartigh, J., C. G. J. M. Hilders, et al.(1993). "Tinnitus suppression by intravenous lidocaine in relation to its plasma concentration." *Clin Pharmaocol & Ther* 54:415–420.
Ochi, K. and J.J. Eggermont (1996). "Effects of salicylate on neural activity in cat primary auditory cortex." *Hearing Research* 95 (1–2): 63–76.
Caspary, D.M., J. C. Milbrandt, et al. (1995). "Central Auditory Aging: Gaba Changes in the Inferior Colliculus." *Experimental Gerontology* 30 (3/4):349–360.
McGeer, E. G. and P. L. McGeer (1975). "Age Changes in the Human for Some Enzymes Associated with Metabolism of the Catecholamines, Gaba and Acetycholine." *Neurobiology of Aging*. J. Ordy, Brizzee KR, New York, Plenum Pres: 287–305.
Raza, A., J. C. Milbrandt, et al. (1994). "Age–Related Changes in Brainstem Auditory Neurotransmitters: Measures of GABA and Acetylcholine Function." *Hear Res* 77 (1–2):221–230.

(List continued on next page.)

*Primary Examiner*—Sharon Kennedy
(74) *Attorney, Agent, or Firm*—Banner & Witcoff, Ltd.

(57) ABSTRACT

A method for treating severe tinnitus is disclosed. The method of the present invention comprises implanting a catheter into a patient and administering a therapeutic agent intrathecally into the patient's cerebrospinal fluid.

36 Claims, 5 Drawing Sheets